US006530376B1

(12) United States Patent
Padget et al.

(10) Patent No.: US 6,530,376 B1
(45) Date of Patent: Mar. 11, 2003

(54) MINIMALLY LIGHT REFLECTIVE SURGICAL DRAPE

(75) Inventors: David B. Padget, Stillwater, MN (US); Leland W. Annett, Stillwater, MN (US); Timothy P. Smalstig, Burnsville, MN (US)

(73) Assignee: Medical Concepts Development, Inc., Woodbury, MN (US)

( * ) Notice: Subject to any disclaimer, the term of this patent is extended or adjusted under 35 U.S.C. 154(b) by 0 days.

(21) Appl. No.: 09/975,646

(22) Filed: Oct. 10, 2001

(51) Int. Cl.[7] .............................................. A61B 19/00
(52) U.S. Cl. ...................................... 128/849; 128/853
(58) Field of Search .................................. 128/849–856

(56) References Cited

U.S. PATENT DOCUMENTS 3,668,050 A * 6/1972 Donnelly ................. 128/853 X
3,669,106 A * 6/1972 Schrading .................... 128/853
3,677,266 A * 7/1972 Green ..................... 128/853 X
3,763,857 A * 10/1973 Schrading ............... 128/835 X

* cited by examiner

*Primary Examiner*—Michael A. Brown
(74) *Attorney, Agent, or Firm*—Nawrocki, Rooney & Sivertson, P.A.

(57) ABSTRACT

A surgical drape manufactured or fabricated from a polymeric film having a low glare finish and a predetermined coloration for reducing the luminous intensity of light reflected from the surface thereof is provided. Such surgical drape thereby minimizes reflectivity therefrom, and thus eye strain and fatigue. The subject invention includes the use of colorants, dyes, pigments, etc. to form translucent polymeric surgical drapes that absorb a selected range of wavelengths from surface reflected light. More particularly, the use of coloring agents in combination with a textured surface yield a surgical drape possessing reduced luminance and glare, thereby mitigating eye strain and fatigue. The preferred range of reflected light, in order of preference, is 625–700 nm, 520–560 nm, 450–520 nm, 400–450 nm, 600–625 nm, and 560–600 nm.

16 Claims, 12 Drawing Sheets

Fig.3

| SAMPLE | AVERAGE GLOSS, 20° GEOMETRY | AVERAGE GLOSS, 60° GEOMETRY | AVERAGE GLOSS, 85° GEOMETRY |
|---|---|---|---|
| RED | 0.4 | 3.2 | 2.0 |
| DARK BLUE | 0.3 | 3.1 | 1.7 |
| POWDER BLUE | 0.4 | 3.1 | 3.0 |
| GREEN | 0.3 | 3.7 | 4.0 |
| ORANGE | 0.4 | 4.1 | 3.0 |
| YELLOW | 0.4 | 4.9 | 3.3 |
| PURPLE | 0.4 | 3.4 | 1.7 |
| CLEAR, MCD D1060 | 0.4 | 4.5 | 3.8 |
| CLEAR, 3M 1060 | 0.6 | 6.6 | 5.6 |

Fig.5

| SAMPLE | AVERAGE GLOSS, 20° GEOMETRY | AVERAGE GLOSS, 60° GEOMETRY | AVERAGE GLOSS, 85° GEOMETRY |
|---|---|---|---|
| MCD D1060, SAMPLE#1 | 0.5 | 4.4 | 1.7 |
| MCD D1060, SAMPLE#2 | 0.4 | 4.6 | 2.6 |
| 3M 1060, SAMPLE#1 | 0.5 | 5.9 | 4.9 |
| 3M 1060, SAMPLE#2 | 0.5 | 6.1 | 4.9 |
| DARK BLUE, SAMPLE#1 | 0.3 | 3.1 | 1.9 |
| DARK BLUE, SAMPLE#2 | 0.3 | 3.1 | 2.1 |
| POWDER BLUE, SAMPLE#1 | 0.5 | 3.6 | 2.0 |
| POWDER BLUE, SAMPLE#2 | 0.5 | 3.6 | 1.7 |
| GREEN, SAMPLE#1 | 0.4 | 3.9 | 2.1 |
| GREEN, SAMPLE#2 | 0.4 | 3.9 | 2.3 |

Fig. 7

|  | AVERAGE | STD DEV | CONFIDENCE INT. C.I./2 | t-TEST |
|---|---|---|---|---|
| MCD D1060 | 2.13 | 0.872410454 | 0.382343148 | 0.191171574 | 4.99555E-07 |
| 3M 1060 | 4.905 | 1.176212141 | 0.515487464 | 0.257743732 |
| DARK BLUE | 1.975 | 0.275454417 | 0.120720716 | 0.060360358 |
| POWDER BLUE | 1.835 | 0.335074619 | 0.146850011 | 0.073425005 |
| GREEN | 2.185 | 0.471460497 | 0.20662257 | 0.103311285 |

MCD D1060

| | |
|---|---|
| MEAN | 2.13 |
| STANDARD ERROR | 0.200144685 |
| MEDIAN | 2 |
| MODE | 1.4 |
| STANDARD DEVIATION | 0.89507424 |
| SAMPLE VARIANCE | 0.801157895 |
| KURTOSIS | 1.532651112 |
| SKEWNESS | 1.048860334 |
| RANGE | 3.7 |
| MINIMUM | 0.6 |
| MAXIMUM | 4.3 |
| SUM | 42.6 |
| COUNT | 20 |
| CONFIDENCE LEVEL(95.0%) | 0.418907769 |

3M 1060

| | |
|---|---|
| MEAN | 4.905 |
| STANDARD ERROR | 0.269841571 |
| MEDIAN | 4.7 |
| MODE | 4.2 |
| STANDARD DEVIATION | 1.206768194 |
| SAMPLE VARIANCE | 1.456289474 |
| KURTOSIS | -1.139786179 |
| SKEWNESS | 0.045520197 |
| RANGE | 3.9 |
| MINIMUM | 2.8 |
| MAXIMUM | 6.7 |
| SUM | 98.1 |
| COUNT | 20 |
| CONFIDENCE LEVEL(95.0%) | 0.564785075 |

DARK BLUE

| | |
|---|---|
| MEAN | 1.975 |
| STANDARD ERROR | 0.063193521 |
| MEDIAN | 2 |
| MODE | 1.8 |
| STANDARD DEVIATION | 0.282610016 |
| SAMPLE VARIANCE | 0.079868421 |
| KURTOSIS | 0.239972978 |
| SKEWNESS | -0.681068081 |
| RANGE | 1.1 |
| MINIMUM | 1.3 |
| MAXIMUM | 2.4 |
| SUM | 39.5 |
| COUNT | 20 |
| CONFIDENCE LEVEL(95.0%) | 0.1322656 |

Fig. 7 Continued

| POWDER BLUE | | GREEN | |
|---|---|---|---|
| MEAN | 1.835 | MEAN | 2.185 |
| STANDARD ERROR | 0.07687139 | STANDARD ERROR | 0.108160456 |
| MEDIAN | 1.8 | MEDIAN | 2.25 |
| MODE | 1.8 | MODE | 2.1 |
| STANDARD DEVIATION | 0.343779305 | STANDARD DEVIATION | 0.483708264 |
| SAMPLE VARIANCE | 0.118184211 | SAMPLE VARIANCE | 0.233973684 |
| KURTOSIS | 1.46018126 | KURTOSIS | 0.269665478 |
| SKEWNESS | -0.917776323 | SKEWNESS | -0.772433594 |
| RANGE | 1.4 | RANGE | 1.9 |
| MINIMUM | 0.9 | MINIMUM | 1 |
| MAXIMUM | 2.3 | MAXIMUM | 2.9 |
| SUM | 36.7 | SUM | 43.7 |
| COUNT | 20 | COUNT | 20 |
| CONFIDENCE LEVEL(95.0%) | 0.160893717 | CONFIDENCE LEVEL(95.0%) | 0.226382506 |

Fig. 8

| | MCD D1060 | 3M 1060 |
|---|---|---|
| MEAN | 2.13 | 4.905 |
| VARIANCE | 0.8011157895 | 1.456289474 |
| OBSERVATIONS | 20 | 20 |
| PEARSON CORRELATION | -0.248650338 | |
| HYPOTHESIZED MEAN DIFFERENCE | 0 | |
| df | 19 | |
| t STAT | -7.423654458 | |
| P(T <=t) ONE-TAIL | 2.49778E-07 | |
| t CRITICAL ONE-TAIL | 1.729131327 | |
| P(T <=t) TWO-TAIL | 4.99555E-07 | |
| t CRITICAL TWO-TAIL | 2.093024705 | |

Fig.11

| SAMPLE IDENTIFICATION | LUMINANCE(fL) | |
|---|---|---|
| | MATTE FINISH | NON-MATTE FINISH |
| MCD D1060 | 6214 | 6106 |
| 3M 1060 | 6675 | 6528 |
| ORANGE FILM | 5283 | 5305 |
| RED FILM | 3908 | 3699 |
| DARK BLUE FILM | 3790 | 3790 |
| POWDER BLUE FILM | 5479 | 5368 |
| GREEN FILM | 4372 | 4660 |
| PURPLE FILM | 3637 | 3624 |
| YELLOW FILM | 5600 | 5624 |

MINIMALLY LIGHT REFLECTIVE SURGICAL DRAPE

TECHNICAL FIELD

The present invention relates to surgical drapes, and more particularly to surgical drapes formed from a polymeric film having a low glare finish and a predetermined coloration for selectively reducing the luminous intensity of light reflected from the surface thereof.

BACKGROUND OF INVENTION

The complete visual system requires light, the eye, and a conscious observer. The visual system is especially well adapted for rapid and precise visual extraction of spatial information from a more or less remote external world, doing so by analysis of the continuously changing patterns of radiant flux impinging upon the surfaces of the eyes. Much of this light is reflected from objects which must be discriminated, recognized, attended to, and/or avoided in the environment, all the while transcending enormous variations in intensity, quality and geometry of illumination as well as the vantage point of the observer.

Light (i.e., visible light) represents only one portion of the electromagnetic spectrum, namely the portion laying between radio waves and x-rays, more particularly those electromagnetic waves possessing a wavelength between about 380–770 nanometers (nm). The lighting or illumination of a surface is the luminous flux which it receives per unit area (i.e., luminous flux is a measure of the power of visible light). Common units for luminous flux (i.e., illuminance) include the foot-candle (i.e., 1 lumen per square foot, or the foot lambert), and the lux (i.e., 1 lumen per square meter). Minimum recommended task based lighting levels are provided by General Electric Company as follows: casual, 30 footcandles (fc); rough, 50 fc; medium, 100 fc; fine, 500 fc; and, extra-fine, 1,000 fc.

Color is a characteristic of light that produces specific degrees of hue, saturation and brightness, with most color models of perceived color containing these three components. For instance, in the International Commission on Illumination (CIE) "L*a*b model", color is modeled as a sphere, with lightness comprising the linear transformation from white to black, and hues modeled as opposing pairs, with saturation being the distance from the lightness axis.

Chromaticity (i.e., apparent color temperature or correlated color temperature) is the measure of a light source's "warmth" or "coolness," expressed in the Kelvin (° K.) temperature scale. It describes the appearance an object would have if it were heated to incandescence (i.e., the point of emitting light) then to higher temperatures where the appearance changes from ruddy red through a range of warm colors to white, then finally to blue-white. Selected sources of illumination and their color temperatures include: candle flame, 1850° K.; sunlight (sunrise/set), 2000° K.; sunlight (mean noon), 5400° K.; 40 watt incandescent tungsten lamp, 2650° K.; 100 watt incandescent tungsten lamp, 2865° K.; 500 watt incandescent tungsten lamp, 2960° K.; photoflood/reflector flood, 3400° K.; white flame carbon arc lamp, 5000° K.; and, xenon arc lamp, 6420° K.

The human eye includes various muscles which, like any part of the human body, will tire and strain when kept in a fixed configuration for sufficiently long periods. Immediate symptoms of eye fatigue and eye strain include headaches and difficulty focusing one's vision. In the long term, prolonged or severe eye fatigue and strain may decrease the strength of eye muscles and require corrective lenses, or an increased prescription for those already requiring corrective lenses.

When an object is too close to a viewer, the viewer is forced to bring his or her eyes inward (i.e., towards their nose). The motion of the eyes turning inward is called convergence. Convergence requires intensive exertion of the eye muscles, in particular the ocular muscles. When the eyes are not properly relaxed through either visual exercise or rest, the viewer may experience eye fatigue and/or eye strain. Repeated and/or prolonged convergence can permanently decrease the strength of the eye muscles.

In addition, a viewer's eyes must focus in order to properly perceive an object. Focusing causes strain to the viewer's eyes. In order to focus on close objects, the eye's lens thickens. That is, the closer an object to the viewer, the thicker the eye's lens must shape themselves. Thickening the eye's lens is particularly exhausting on the eye muscles, serving to exacerbate the fatigue and strain brought on by the convergence that also accompanies viewing close objects.

One result of eye fatigue and eye strain is a diminished synchronization between a viewer's pair of eyes. That is, the viewer's left and right eyes are not working synchronously to provide the visual information required to visually perceive one's surroundings. Accordingly, common orthoptic tests involve monitoring the eye's ability to synchronize, while common orthoptic treatments involve the viewer performing eye exercises that promote synchronization, either through stretching and strengthening the eye muscles, or via forced relaxation.

Some of the most common causes of eye fatigue and/or strain include viewing close objects, viewing objects displayed on a light emitting medium, and simply viewing images for excessive time periods. Reading or doing close work in extreme light conditions, whether bright or dim, for extended periods forces the eyes to focus under less than optimal conditions, and thereby contributes to eye strain, symptoms of which may include; headaches; blurred vision; pain or soreness of the eyeball; red/watery eyes; dry eyes that feel scratchy; tired, aching heaviness of the eyelids or forehead; back and neck aches; and, muscle spasms.

Glare is a similar phenomenon which contributes to eye strain, in addition to mitigating visual acuity. The contrast between the image being viewed and its background is reduced by reflected light, making it harder for the brain to interpret the image. Facial and eye muscles tighten as the eye unconsciously strains to send a clear signal to the brain.

A particularly harsh visual system setting, or environment, for the eyes is a hospital operating room. In addition to the requirements of up-close high precision work, which in and of itself is stressful, high intensity surgical lighting systems are present to aid the surgeon and his or her team. Such lighting systems are known to deliver up to, and in excess of 140,000 lux (i.e., lumens per square meter, or about 13,000 fc) at about 4500° K. chromaticity. Working for long periods of time, anywhere from one to eight plus hours per procedure, under such light conditions is more often than not the cause of eye fatigue and/or strain. Alleviation or mitigation of the source of such stress to the visual system would be most welcome. Such improved working conditions, as minimal as they might seem, may be of paramount importance to those who rely upon the skill and execution of the surgeon.

SUMMARY OF THE INVENTION

A surgical drape manufactured or fabricated from a polymeric film having a low glare finish and a predetermined coloration for reducing the luminous intensity of light reflected from the surface thereof is provided. Such surgical drape thereby minimizes reflectivity therefrom, and thus eye strain and fatigue. The subject invention includes the use of colorants, dyes, pigments, etc. to form translucent polymeric surgical drapes that absorb a selected range of wavelengths from surface reflected light. Furthermore, the subject invention includes such energy absorbing drape having a textured surface to effectuate a reduced reflectivity. More particularly, the use of coloring agents in combination with a textured surface yield a surgical drape possessing reduced luminance and glare, thereby mitigating eye strain and fatigue. The preferred range of reflected light, in order of preference, is 625–700 nm, 520–560 nm, 450–520 nm, 400–450 nm, 600–625 nm, and 560–600 nm. More specific features and advantages will become apparent with reference to the DETAILED DESCRIPTION OF THE INVENTION, appended claims, and the accompanying drawing figures.

BRIEF DESCRIPTION OF THE DRAWINGS

FIG. 3 is a tabulation of Test No. 1 data, namely average gloss values, as a function of geometry, for each of the test drape samples;

FIG. 5 is a tabulation of Test No. 2 data, namely average gloss values, as a function of geometry, for each of the test drape samples;

FIG. 7 is a tabular summary of statistical parameters associated with the obtained gloss data;

FIG. 7 Continued is a continuation of the tabular summary of FIG. 7;

FIG. 8 is a tabular comparison of t-Test results for the drape of the subject invention and the benchmark drape;

FIG. 11 is a tabulation of luminance, as a function of drape finish, for each of the test drape samples; and, FIG. 12 is a graphic representation of the data of FIG. 11.

DETAILED DESCRIPTION OF THE INVENTION

Figure 1:
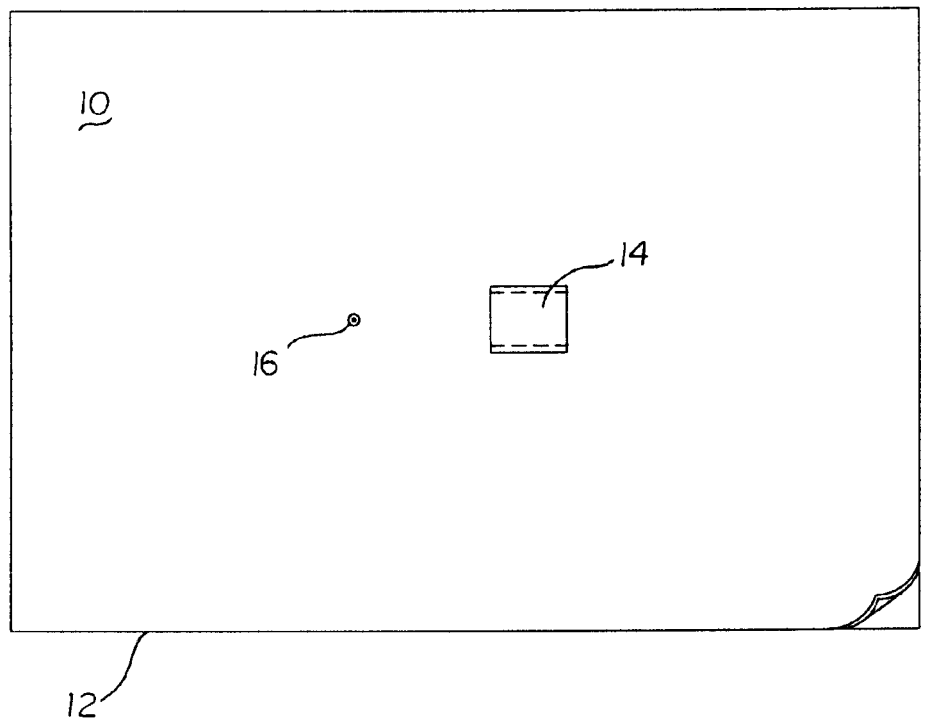
FIG. 1 is a plan view of a surgical drape of the subject invention, more particularly an ocular drape.
Figure 2:
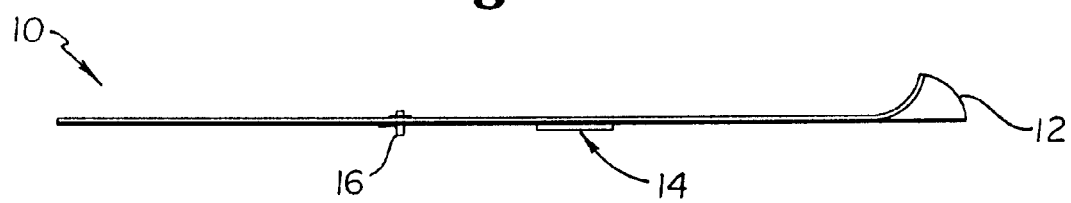
FIG. 2 is a side or edge view of the surgical drape of FIG. 1.

Referring to FIGS. 1 and 2, there is shown a surgical drape 10, more particularly an ophthalmic incise drape, having a perimeter edge 12, an adhesive patch 14, and a drain port assembly 16. These figures are provided to illustrate one embodiment of the subject invention. Although an ophthalmic drape is shown, it is to be understood that the present invention is not so limited, with any drape style or configuration being formed, treated, otherwise manufactured, etc., as is known to those of skill in the pertinent art, so as to reduce eye strain consistent with the invention of the subject disclosure. Drape styles suitable for the practice of the subject invention include, but are not limited to, those disclosed in U.S. Pat. Nos. 4,745,915 and 6,102,044, each of which being incorporated herein by reference.

The subject invention includes the use of colorants, dyes, pigments, etc. to form translucent polymeric surgical drapes that absorb a selected range of wavelengths from surface reflected light. Furthermore, the subject invention includes such energy absorbing drape having a textured surface to effectuate a reduced reflectivity. More particularly, the use of coloring agents in combination with a textured surface yield a drape possessing reduced luminance and glare, thereby mitigating eye strain and fatigue. Test results, which are discussed hereinafter, indicate that the preferred range of reflected light be, in order of preference, 625–700 nm, 520–560 nm, 450–520 nm, 400–450 nm, 600–625 nm, and 560–600 nm.

Colored drape line testing was conducted to demonstrate the reduction in both glare and light reflection utilizing the colored polyethylene surgical drapes. Both specular gloss testing, illuminance, and chromaticity testing was completed. A discussion of each methodology and the results obtained follows.

Specular Gloss Testing

Specular gloss testing was performed in accordance with ASTM Standard D523-89, which is incorporated herein by reference, on differing polyethylene drape materials. A specular gloss test measures the capacity of a surface to reflect more light in one direction than in others. The main factors that affect the reflection of light from a surface are the haziness of the material and the texture of the surface. The specular gloss test is performed using an apparatus that consists of an incandescent light source and a photo detector. The angle of the incident light is measured from the perpendicular of the material surface. The photo detector is placed at the mirror/image position of the light source. Measurements of the luminous flux are taken at 85°, 60°, and 20° geometries. The values that are obtained from the measurements are the relative luminous reflectance factor (RLRF). The RLRF is the ratio of the luminous flux from the surface being tested to the luminous flux of a standard polished glass mounted on a black surface measured at the same angle.

Since the results from this test are mainly affected by the surface finish of material, it is expected that the difference between specular gloss readings for the benchmark drapes (i.e., a Minnesota Mining & Manufacturing, Inc. model No. 1060 (hereinafter 3M® 1060), and a Medical Concepts Design Inc., model No. D1060 (hereinafter MCD D1060)) to be greater than the difference between the colored drape materials. This is primarily due to the fact that the surface finish of the benchmark drapes are different. The difference in the specular gloss readings between the colored drapes and the MCD D1060 drape should not be as great since they have a similar surface finish. The MCD D1060 drape and the colored drape should have lower specular gloss numbers since, when observed visually, they appear to have much less glare than the 3M® 1060 drape.

In a first study (i.e., Test No. 1), nine different drape samples were tested, and ten readings were taken for each drape sample. The results of the testing are presented in FIGS. 3 and 4.

Figure 4:
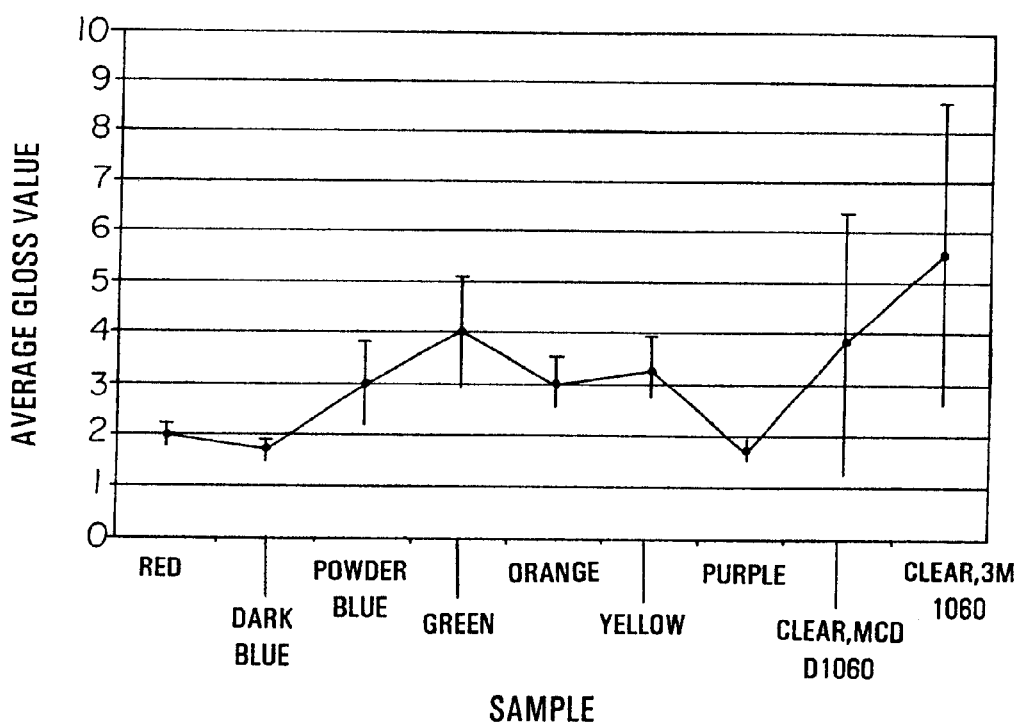
FIG. 4 is a graph of the average gloss values at an 85° geometry recorded for each of the test drape samples of the table of FIG. 3.

Section 4 of ASTM D523 indicates that an 85° geometry is the most useful for comparing different specimens when the gloss value at 600 is less than 10. The graph of FIG. 4 shows the average gloss values for each specimen at a 85° geometry. The graph of FIG. 4 also has standard deviation bars of +/−σ centered on the average value. From this graph, it can be seen that the benchmark MCD D1060 drape and the colored drapes, which have a similar surface texture, are all within a narrow range of values (1.7–3.8). The benchmark 3M® 1060 drape is outside the aforementioned range (5.6), indicating that its gloss value was significantly higher than that of the benchmark MCD D1060 drape.

A second specular gloss study (i.e., Test No. 2) was performed using those drape colors which yielded the lowest average gloss value in the first study. Also included were the benchmark MCD D1060 and the benchmark 3M® 1060 drape for comparison. In the second study, two different samples of each drape material were tested and the measurements were all taken on the matte finish side. The results are presented in FIGS. 5 and 6.

Figure 6:
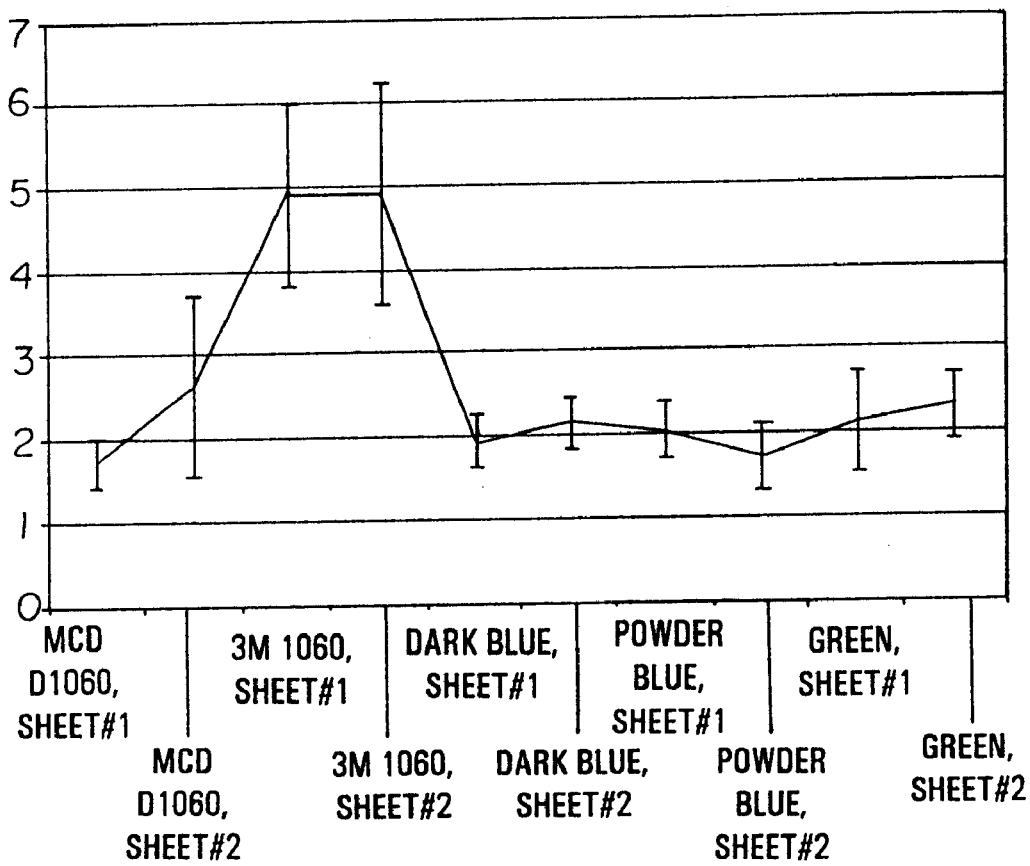
FIG. 6 is a graph of the average gloss values at an 85° geometry recorded for each of the test drape samples of the table of FIG. 5.
Figure 9:
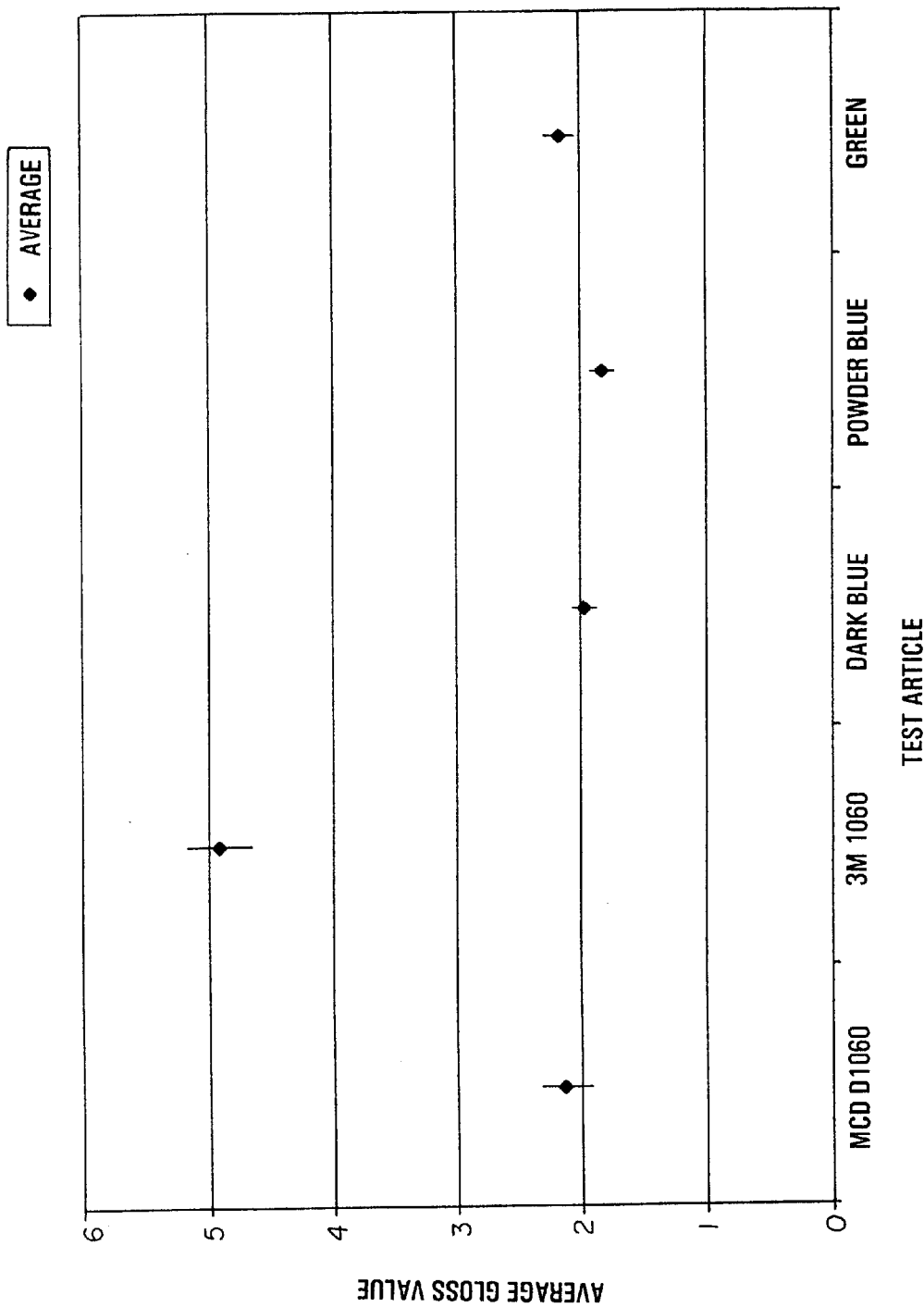
FIG. 9 is a graph depicting the average (mean) gloss values at an 95% confidence interval recorded for each of the test drape samples of the table of FIG. 7.
Figure 10:
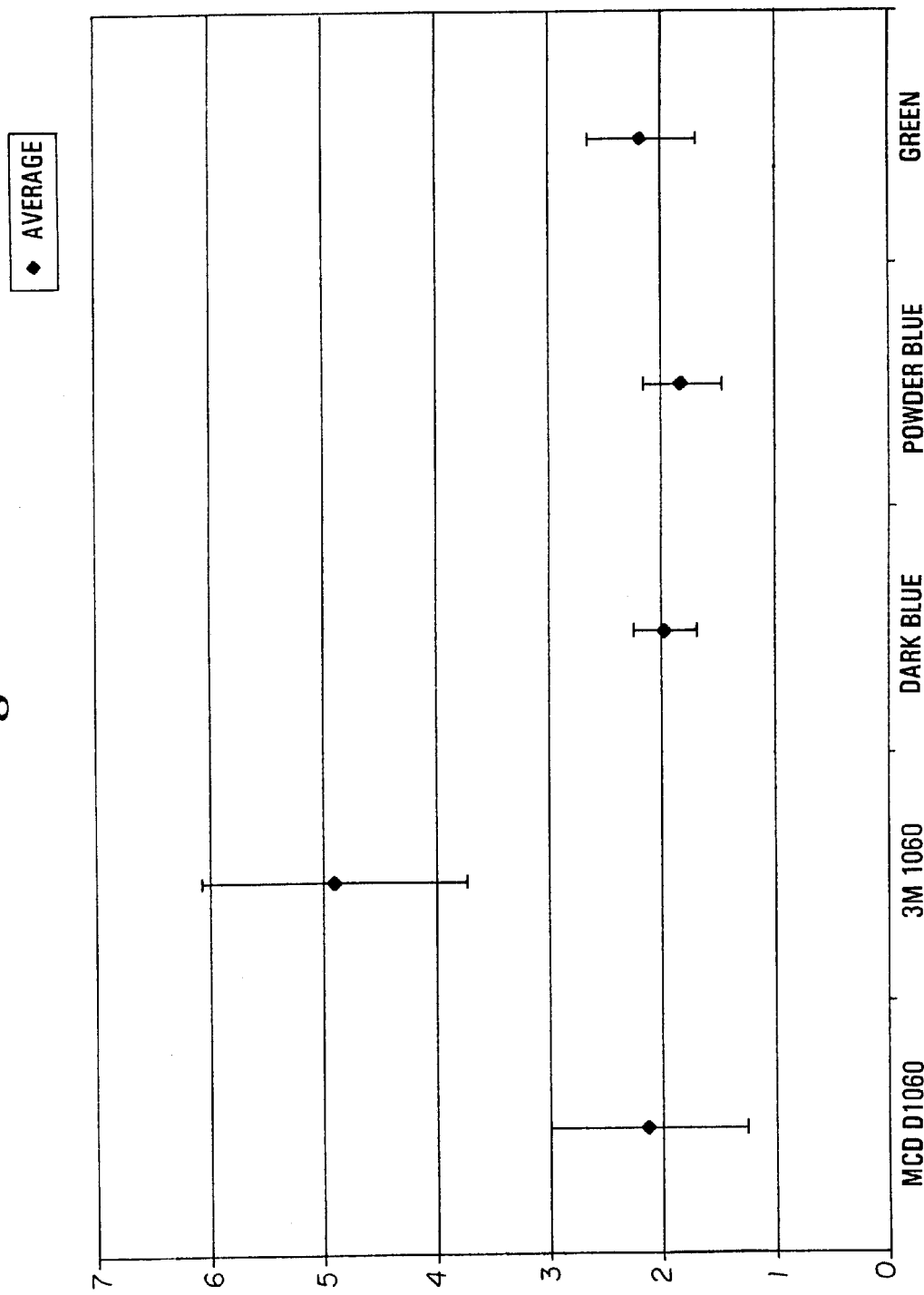
FIG. 10 is a graph depicting the standard deviation of the gloss values recorded for each of the test drape samples of the table of FIG. 7.

Once again, the values of the 60° geometry were below 10, so the 85° geometry values were used for the comparison purposes. The graph of FIG. 6 shows the average gloss values for each specimen at a 85° geometry. The graph of FIG. 6 also has standard deviation bars of +/−σ centered on the average value. From this graph, it can be seen that there is little difference between the benchmark MCD D1060 drape material and the colored drape material. Once again, these materials have very similar surface texture. It is further clear from the graph of FIG. 6 that the gross values for the benchmark 3M® 1060 drape samples are higher than those of the benchmark MCD D1060 drape and colored drapes. Both samples of the benchmark 3M® 1060 drape have the same average gloss value (i.e., 4.9). The average gloss values for the samples of the benchmark MCD D1060 drape and colored drape materials are between 1.7 and 2.6. The clear MCD drape samples have values at both extremes of this range, and all the gloss values for the colored drapes fell between these two extremes, indicating that color was not a factor. Since the main difference between all of these materials is surface texture, it is apparent that the rougher (i.e., less smooth) surface finishes of the MCD D1060 and the colored drape materials reduce glare significantly when compared to the benchmark 3M® 1060. There seems to be no correlation between the color of the drape material and glare reduction since the gloss value difference between the benchmark MCD D1060 clear drape and the colored drapes is not very significant.

Results of a statistical analysis of gloss data are generally presented in FIGS. 7–10. Values for tabulated statistical parameters are found in FIG. 7, tabulated t-Test results for the MCD D1060 and 3M® 1060 drapes are found in FIG. 8, with mean and standard deviation gloss readings for noted test articles illustrated in FIGS. 9 and 10 respectively.

Illuminance and Chromaticity Testing

Illuminance and chromaticity testing was performed to measure the differences between the colored and clear drape materials. The illuminance test measures the amount of light that was reflected from the drapes' surface. The chromaticity test measures the hue and saturation of the light reflected from the surface. The tests were performed on the matte and non-matte finished sides of the drape materials. The test was performed using a PR-703 photo research spectra radiometer. The samples were placed in the same standard surface and a xenon light source was used to illuminate the material. The light source was perpendicular to the surface of the material. The detector was at a 10° angle from the light beam since it could not physically occupy the same space as the light source.

Figure 12:
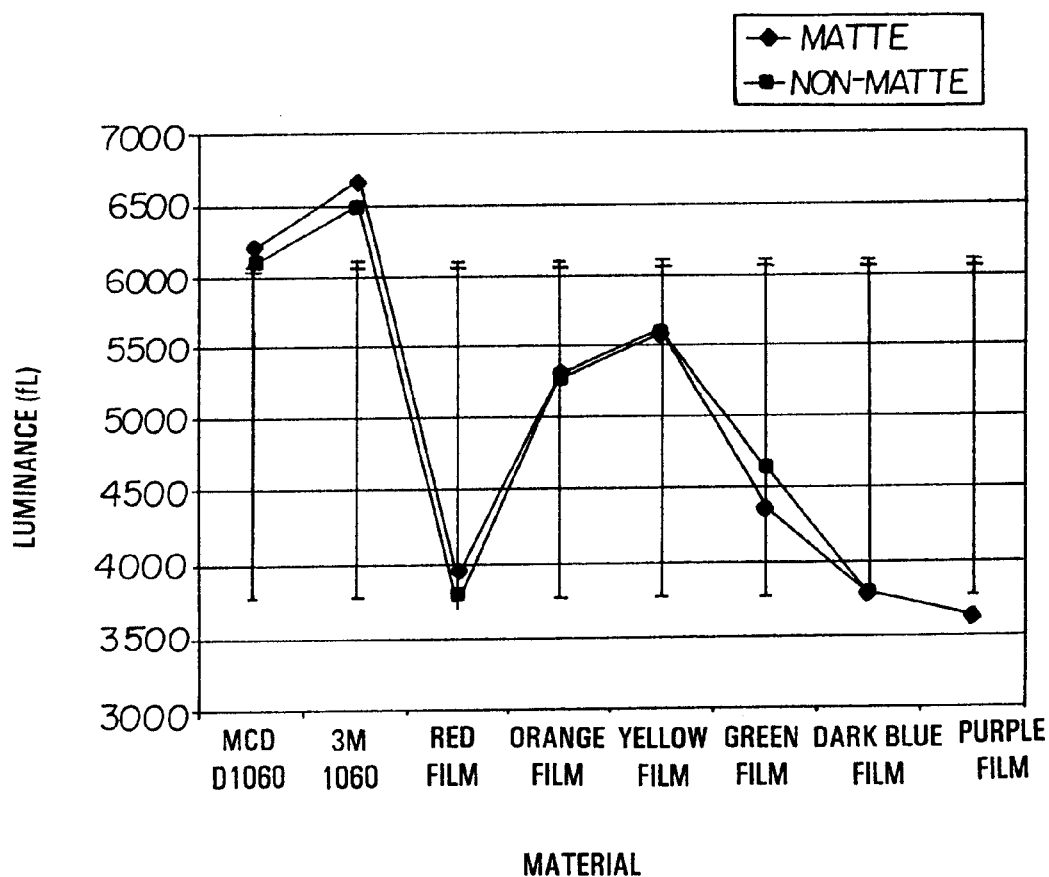

As the objective of the illuminance and chromaticity testing is to find the material colors that most reduce the intensity of reflected light, determination of luminance value (i.e., a measurement of luminous intensity of light being reflected from the surface of the material in a given direction per unit area of projected area of the source, as viewed from that direction) is critical. The results of the illuminance test are presented in FIGS. 11 and 12.

The results of this test indicate that there is a difference between the different drape material colors when it comes to the amount of light reflected. The wide standard deviation bars (+/−σ centered about the average value calculated from the data point on the graph) indicate this large difference. The highest value was for the benchmark 3M® 1060 drape. It had luminance values of 6,675 foot lambert (fL) on the matte side and 6,528 fL on the non-matte side. The benchmark MCD D1060 drape was also above the 6,000 fL value. The lowest values were associated with films colored red, dark blue, and purple (i.e., violet), with their luminance values ranging from 3,637 to 3,908 fL for the matte finish side of the film, and 3,624 to 3,790 fL for the non-matte side of the film. They were substantially lower than all other film colorations. From this information it is concluded that the intensity of the light reflected was lowest for the dark colors, and highest for the two benchmark drapes. This test also supports the notion that the color of the drape material plays a much great role in the intensity of the reflected light. The finish of the film has minimal effect on the intensity of reflected light, as shown by the very close values associated with the matte and non-matte finish sides of each of the films. On the graph of FIG. 12, the standard deviation bars of +/−σ centered on the average value of all the data points for the matte and non-matte finish sides are indicated. The average for both is almost the same, and the standard deviation for both almost identical, indicating that the surface finish of the film does not affect the intensity of the reflected light.

The colored drape line testing indicates that the surface finish of the film has the greatest effect on glare. The rougher the surface finish, the less glare. Color has very negligible effect on glare. Furthermore, the color of the film has the greatest effect on the reduction of the intensity of the light reflected from the film surface. The darker colors, towards the red and violet ends of the spectrum, performed best. The colors in the middle of the visible spectrum did not perform as well, with the two white colored benchmark drapes being the least effective. The surface finish of the film had no effect on the amount of light reflected. In summary, the color of the film controls the intensity of the light reflected, and surface finish of the film controls the glare.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A surgical drape comprising a polymeric film having a low glare finish and a predetermined coloration for reducing the luminous intensity of light reflected from the surface thereof, said surgical drape thereby minimizing reflectivity and potential eye strain.

2. The surgical drape of claim 1 wherein said energy absorbing polymeric film reflects light having a wavelength in the range of about 4,000 to 4,500 angstroms.

3. The surgical drape of claim 1 wherein said energy absorbing polymeric film reflects light having a wavelength in the range of about 4,500 to 5,200 angstroms.

4. The surgical drape of claim 1 wherein said energy absorbing polymeric film reflects light having a wavelength in the range of about 5,200 to 5,600 angstroms.

5. The surgical drape of claim 1 wherein said energy absorbing polymeric film reflects light having a wavelength in the range of about 6,250 to 7,000 angstroms.

6. The surgical drape of claim 1 wherein said low glare finish is a matted surface.

7. The surgical drape of claim 1 wherein said low glare finish is a textured surface.

8. The surgical drape of claim 1 wherein said luminous intensity is reduced by up to about 45%.

9. The surgical drape of claim 1 wherein said polymeric film comprises a polyolefin.

10. The surgical drape of claim 1 further comprising a coating of an adhesive composition overlying at least a portion of said polymeric film.

11. The surgical drape of claim 10 further comprising a release liner, said release liner overlaying said coating of an adhesive composition for selective removal therefrom.

12. The surgical drape of claim 11 further comprising an antimicrobial agent carried by said polymeric film, said antimicrobial agent being carried by said polymeric film on a side opposite said coating of an adhesive composition.

13. In a method of producing a surgical drape, the steps comprising:

(a) selectively adding coloration to a polymeric drape starting material;

(c) forming a surgical drape from the colored polymeric drape starting material so as to produce a translucent, energy absorbing polymeric surgical drape capable of reducing the luminous intensity of light being reflected from the surface thereof, thereby substantially eliminating eye strain.

14. In the method of claim 13, the further step of providing a low glare finish to at least one side of said translucent, energy absorbing polymeric surgical drape.

15. In the method of claim 14 wherein said low glare finish is a matted surface.

16. In the method of claim 14 wherein said low glare finish is a textured surface.

* * * * *